United States Patent
Campbell

(10) Patent No.: US 11,486,807 B2
(45) Date of Patent: Nov. 1, 2022

(54) WATER ACTIVITY TRACKING FOR LOSS DETECTION

(71) Applicant: METER Group, Inc. USA, Pullman, WA (US)

(72) Inventor: Scott H. Campbell, Pullman, WA (US)

(73) Assignee: METER Group, Inc. USA, Pullman, WA (US)

( * ) Notice: Subject to any disclaimer, the term of this patent is extended or adjusted under 35 U.S.C. 154(b) by 315 days.

(21) Appl. No.: 16/923,963

(22) Filed: Jul. 8, 2020

(65) Prior Publication Data

US 2022/0011153 A1    Jan. 13, 2022

(51) Int. Cl.
*G01N 5/04* (2006.01)
*G01N 33/00* (2006.01)
*G01N 7/16* (2006.01)

(52) U.S. Cl.
CPC .............. *G01N 5/045* (2013.01); *G01N 7/16* (2013.01); *G01N 33/0098* (2013.01)

(58) Field of Classification Search
CPC ....... G01N 5/045; G01N 7/16; G01N 33/0098
See application file for complete search history.

(56) References Cited

U.S. PATENT DOCUMENTS 6,279,387 B1 * 8/2001 Kikuchi ................. G01N 5/025
177/61

FOREIGN PATENT DOCUMENTS

CN    110146401 A * 8/2019 ............... G01N 5/00

OTHER PUBLICATIONS

"Measuring Moisture Content of Pharmceutical Products Using Water Activity", Published online by Decagon Devices in 2009 and as downloaded by the Internet Archive wayback Machine on Jul. 12, 2018 at http://manuals.decagon.com/Application%20Notes/13936_MC%20of%20Pharm%20Products%20by%20Aw_Print.pdf.*

* cited by examiner

*Primary Examiner* — Justin N Olamit
(74) *Attorney, Agent, or Firm* — Dorsey & Whitney LLP

(57) ABSTRACT

Systems and methods include testing the weight and water activity of a product at different times and using those measurements to track changes in the water content/water weight and non-water content/non-water weight in the product. These can be useful to detect anomalous activities or batches of processed product, such as when portions of a product are being stolen or improperly altered or wasted. Plant operators can track properties of a product as the product undergoes processing to detect stages and areas in which problems occur and can thereby improve plant and operator efficiency.

18 Claims, 4 Drawing Sheets

WATER ACTIVITY TRACKING FOR LOSS DETECTION

TECHNICAL FIELD

The present disclosure generally relates to methods and systems for tracking weight changes in products that are processed by drying, curing, or other related steps, and the present disclosure specifically relates to methods and systems for using weight and water activity measurements to determine the nature of weight changes in products to detect loss.

BACKGROUND

Food, pharmaceutical, drug, and herb goods are often processed in plants and facilities where raw materials are modified and packaged for consumer use. For some high-value materials, such as controlled and regulated substances, the quantity of the product being processed and any waste is closely monitored on a step-by-step basis. For example, the weight of a batch of cannabis is conventionally measured before it is dried, after it is dried, before it is cured, after it is cured, and so on, at substantially every step in the production process. In this manner, the properties of the batch of material are tracked so that regulators and plant administrators can determine if there is excessive loss of the material being processed caused by wastage, error, or theft.

Although the weight of a product is tracked between stages, bad actors can still try to take advantage of the loss prevention systems in place and find ways to use fake or otherwise unnaturally and maliciously altered measurements to cover stealing, mistakes, or other losses of the product. These improper actions can be difficult to detect and counteract in typical plant conditions. Furthermore, the batch weight of a product can naturally change over time due to water loss such as drying, so even batches that have been maliciously altered can appear on paper to have normal characteristics due to water weight changes. For this and other reasons, there is a constant need for improvements in the field of processing products and detecting product losses while they are processed.

SUMMARY

One aspect of the present disclosure relates to a method comprising measuring a first weight value of a product in a first span of time, measuring a first water activity value of the product in the first span of time, measuring a second weight value of the product in a second span of time, with the second span of time being after the first span of time, measuring a second water activity value of the product in the second span of time, determining a change in water weight of the product between the first span of time and the second span of time based on the first and second water activity values, and determining a change in non-water weight of the product between the first span of time and the second span of time based on the first and second weight values of the product and based on the change in water weight of the product.

In some embodiments, the method can further comprise altering the product between the first and second spans of time. Altering the product can comprise drying, dividing, or curing the product. Measuring the first or second water activity value can comprise removing a sample portion from the product and measuring the water activity of the sample portion. A user can operate tools to measure the first weight value, the first water activity value, the second weight value, and the second water activity value, and at least the change in non-water product weight can be hidden from the user. In some configurations, the method can further comprise producing a signal representative of the change in non-water weight. Furthermore, in some cases the method can further comprise positioning the product in a closed chamber for the first span of time or the second span of time. The method can also comprise detecting a loss indicator of the product based on the change in non-water weight.

Another aspect of the disclosure relates to a non-transitory computer-readable medium having computer-executable instructions stored thereon that, if executed by one or more processors of a computing device, cause the computing device to perform one or more acts of the methods described above or elsewhere herein.

Yet another aspect of the disclosure relates to a computing device comprising a processor, a memory device comprising computer-executable instructions that, if executed by the processor, cause the computing device to perform one or more acts of the methods described above or elsewhere herein.

The above summary of the present invention is not intended to describe each embodiment or every implementation of the present invention. The Figures and the detailed description that follow more particularly exemplify one or more preferred embodiments.

BRIEF DESCRIPTION OF THE DRAWINGS

The accompanying drawings and figures illustrate a number of exemplary embodiments and are part of the specification. Together with the present description, these drawings demonstrate and explain various principles of this disclosure. A further understanding of the nature and advantages of the present invention may be realized by reference to the following drawings. In the appended figures, similar components or features may have the same reference label.

Figure 1:
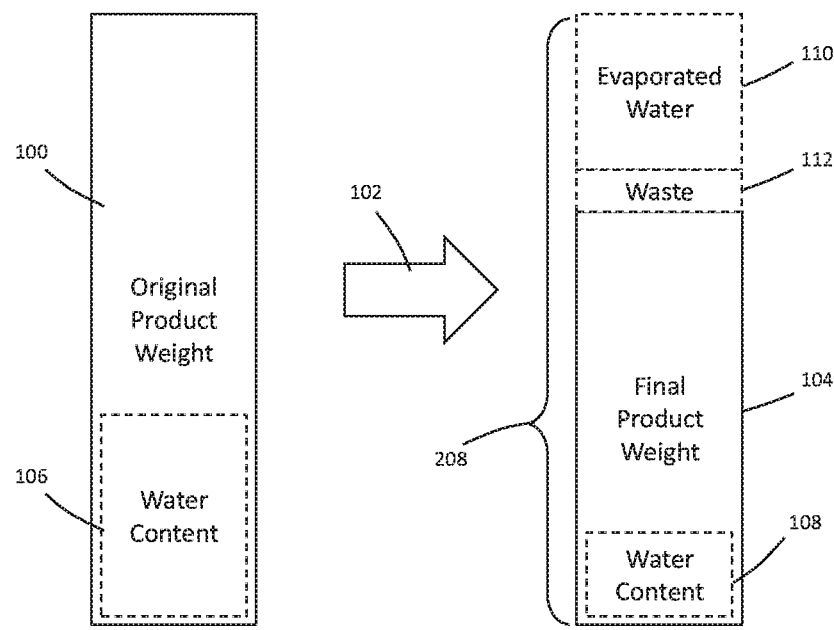
FIG. 1 is a diagram illustrating changes to properties of a product as a result of processing and altering the product.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

As mentioned above, producers of foods, drugs, pharmaceuticals, herb goods, and related products can greatly benefit from detecting indicators of loss of a product (e.g., changes in weight of the product) and differentiating those indicators from natural changes in the characteristics of the product as batches of the product are being processed in a plant or other facility over time. Embodiments of the present disclosure can provide ways to differentiate a loss of water weight of a product, such as loss of water during a drying or curing process, from loss of weight of other parts of the product, such as loss of husks, residues, seeds, oils, fibers, meat, powders, or other portions of the product. These embodiments can include measuring and recording the weight and water activity of the product or a batch thereof at each processing act, converting the water activity measurements to water weight measurements (and/or related water content measurements), and comparing the change in water weight to the change in overall weight to determine a non-water weight change. Non-water weight changes can be evaluated to determine if they are result from common errors, normal wastage or loss of the product while it is processed, laboratory sample removal for testing, or theft or other illicit activity. Accordingly, the user can calculate whether a change in overall weight of the product is caused by water weight change (e.g., drying) or non-water product loss.

The tracking and documenting of these values can provide, for example, improved protection to plant operators and improved assurance to regulators that high-value or controlled substances are being properly managed at the plant. For example, the water activity values, and consequent water weight values determined using the water activity, can be significantly more difficult for employees or other workers to alter or change in a way that is not easily detectable using the principles of the present disclosure.

Accordingly, in one example embodiment, a water activity meter, a scale or balance and a computing device are used to capture data about a batch of the product or a sample taken from the batch of the product as it is being processed, calculate properties of the batch using that data, and compare expected values with the measured values. The software can comprise routines for alerting users (e.g., plant operators) of potential theft or other loss incidents for investigation.

In a cannabis processing facility there are typically only four potential sources of mass loss for a batch: (1) evaporation/drying of the product, (2) intentional separation or division of the product to discard portions of the product or to send the separated portion to byproduct processing (e.g., stems, trimming, leaves, very small portions lost in tools or falling onto a floor and discarded, etc.), (3) quantities lost or removed for laboratory testing (e.g., water activity testing), and (4) theft (e.g., by an employee). Thus, according to some embodiments of the present disclosure, during post-harvest processing of cannabis, each time the weight of the product is taken, a water activity reading can also be taken. By comparing the last water activity reading for a batch with a current reading, the amount of water loss due to drying or evaporation since the last reading can be determined. Then, by comparing the weight readings, the system or user can determine whether the measured water activity value is consistent with the measured weight loss. If the water activity is the same, but the batch shows a measurable weight loss nonetheless, a potential product loss incident has be detected and can be investigated.

Similarly, when cannabis enters a trimming stage, the weight and water activity of the batch can be measured before the act of trimming takes place, and then the weight in water activity of the flower portion of the product and the trim portion of the product can be taken separately. Any loss of moisture in the act of trimming can be calculated by comparing the water content indicated by the water activity readings. Mass lost to evaporation plus mass lost to trimming plus the finished flower weight should equal the mass of the batch at the beginning of the trimming. Otherwise, some of the measurements can be deemed as potentially problematic. Additional embodiments and use cases are described below in connection with the figures.

The present description provides examples, and is not limiting of the scope, applicability, or configuration set forth in the claims. Thus, it will be understood that changes may be made in the function and arrangement of elements discussed without departing from the spirit and scope of the disclosure, and various embodiments may omit, substitute, or add other procedures or components as appropriate. For instance, the methods described may be performed in an order different from that described, and various acts or steps may be added, omitted, or combined. Also, features described with respect to certain embodiments may be combined with or used in other embodiments.

FIG. 1 is a block diagram illustrating example weight measurements taken when processing a product that changes weight and water content during a processing action. The original product weight 100 can be measured at the start of or prior to the processing act, then the processing action 102 can take place, and a final product weight 104 can be taken at the conclusion of or after performing the processing action 102. The original product weight 100 can be different in magnitude than the final product weight 104 due at least in part to a reduction of the original water content 106 over the course of the processing action 102, as indicated by the original product weight 100 being shown with a larger block than the final product weight 104. In some embodiments, the change in water content in the product can occur due to evaporation, drying, or other natural processes occurring during the processing action 102, as indicated by the evaporated water 110. As a result, the final weight 104 can be less than the original weight 100 due to loss of water weight 110. Additionally, a small amount of weight change can be due to wastage of the product while it is being processed or measurement error in the tools used to obtain the weight measurement, as collectively indicated by waste portion 112.

The magnitude of the change in weight from the original weight 100 to the final weight 104 can vary significantly depending on environmental conditions in the plant or the processing action 102 takes place. A processing location with high humidity can have a smaller change in water weight attributable to evaporation, and the location with lower humidity can have a relatively larger change in water weight attributable to evaporation due to the interaction between the vapor pressures of the product and its surroundings. In some embodiments, the water content of the product can increase due to absorption of ambient moisture or water intentionally applied to the product as part of the processing action 102.

Thus, variations in the change in weight across the processing action 102 can be dependent upon the geographic location of processing, the internal environment of the processing location (e.g., relative humidity and temperature of the location), the seasons in which the product is being processed (e.g., due to the water content of the product being different in various seasons), the weather at the plant site (e.g., causing additional airflow in the plant), the type of processing taking place (e.g., cool drying versus heated drying), similar factors, and combinations thereof. Without knowledge of the water content (e.g., 106, 108), a plant administrator or operator will be uncertain regarding whether the change in weights 100, 104 is due to these environmental conditions causing water loss or due to loss of non-water portions of the product (e.g., due to theft or excess wastage, as discussed in connection with FIG. 2).

Figure 2:
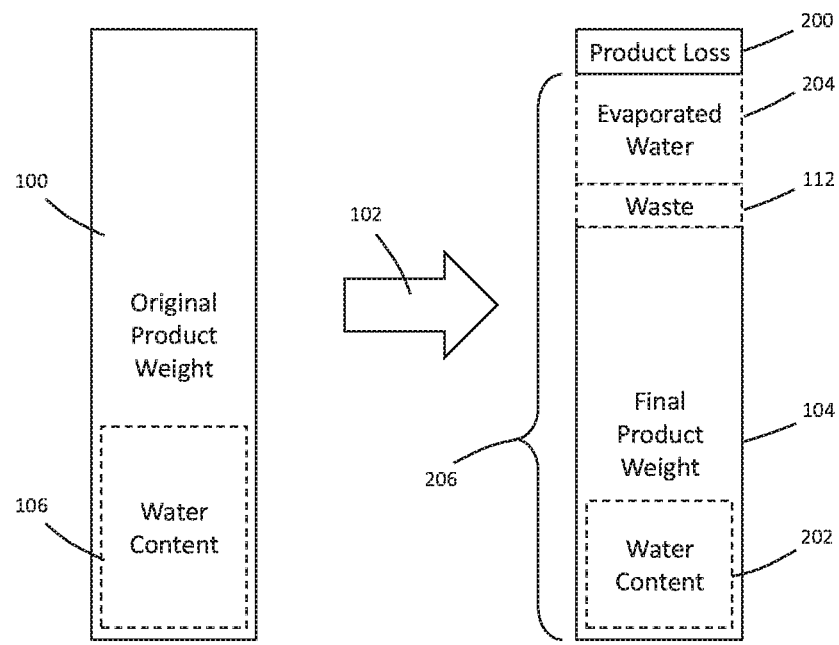
FIG. 2 is a diagram illustrating another type of change to properties of a product as a result of processing and altering a product that includes product loss.

FIG. 2 shows an example embodiment in which the original product weight 100 and the original water content 106 are the same as in FIG. 1, the product undergoes the same processing action 102, and the final product weight 104 and waste 112 are equal to the final product weight 104 and waste 112, respectively, in FIG. 1. Therefore, a plant operator who merely tracks the weight of the product at the start and end of each processing action 102 would not see any difference between the results of the process in FIG. 1 and the results of the process in FIG. 2 because the difference between the original product weight 100 and the final product weight 104 is the same in each case. An unwary supervisor would rationally assume there is no improper product loss since the measurements are the same.

However, as shown in FIG. 2, a portion of the change in weight of the product can be attributed to product loss 200, such as theft of the product while it was being processed, excessive waste, faulty equipment, or other problematic or suspicious factors. Undetected product loss 200 can significantly impact the efficiency of the plant. The product loss 200 may go unnoticed because the final product weight 104 includes higher water content 202 as compared to the water content 108 in the previous example. Thus, although the final non-water quantity of the product has been reduced relative to the final non-water quantity of the product in FIG. 1 (as indicated by the area within box 104 that is not occupied by box 108), the increased water content 202 (relative to water content 108) offsets the non-water weight difference, thereby making the overall final product weight 104 equal in FIGS. 1 and 2. The weight of the evaporated water 204 is also less than the evaporated water weight 110.

By using embodiments of the systems and methods disclosed herein, the plant operator can detect and compare the water content values of the product before and after the processing action 102 and can thereby determine the weight of the product lost to evaporation (e.g., 204) and how much of the weight of the product is still attributable to water content in the product (e.g., 202). With this information, the total expected weight 206 of the final product (i.e., 104), normal waste (i.e., 112), and the lost water weight (i.e., 204) can be calculated and compared to the original product weight 100. If there is any discrepancy between the magnitude of the total expected weight 206 and the magnitude of the original weight 100, that discrepancy can be detected as potentially being a product loss 200 to investigate and mitigate. By comparison, in FIG. 1, the total expected weight 208 would be equal to the original product weight 100 because the magnitudes of the final product weight 104, waste 112, and evaporated water 110 add up the original product weight 100. Embodiments of the present disclosure can therefore beneficially help plant operators and other interested parties to identify when and how product loss 200 occurs.

Figure 3:
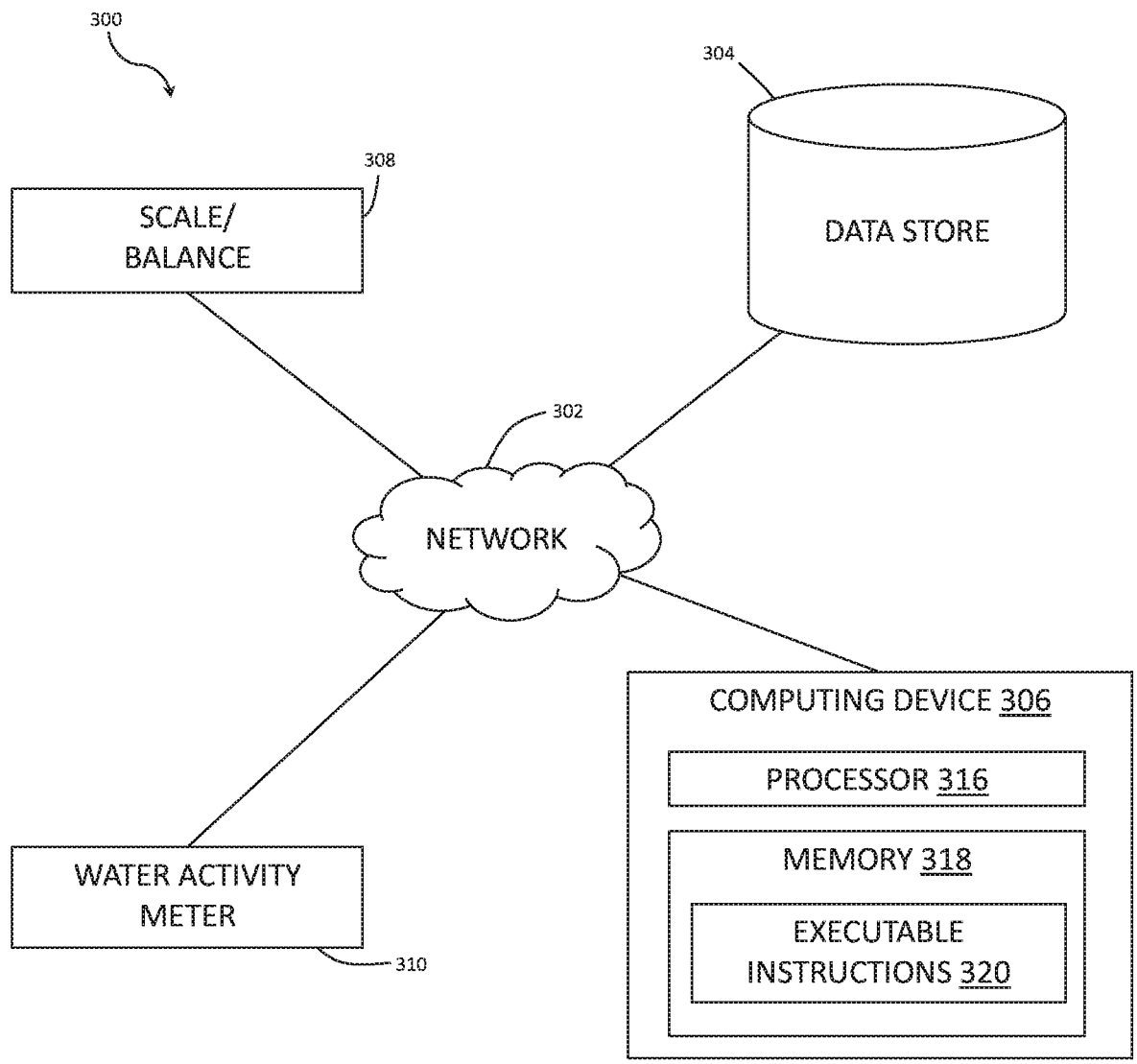
FIG. 3 is a diagram of a system according to an embodiment of the present disclosure.

FIG. 3 is a schematic illustration of a system 300 for improving detection of product loss in accordance with examples described herein. It should be understood that this and other arrangements and elements (e.g., machines, interfaces, function, orders, and groupings of functions, etc.) can be used in addition to or instead of those shown, and some elements may be omitted altogether. Further, many of the elements described may be implemented as discrete or distributed components or in conjunction with other components, and in any suitable combination and location. Various functions described herein as being performed by one or more components may be carried out by firmware, hardware, and/or software. For instance, and as described herein, various functions may be carried out by a processor executing instructions stored in memory.

Among other components not shown, system 300 of FIG. 3 includes at least one data store 304, at least one computing device 306, at least one scale or balance 308, and at least one water activity meter 310. Computing device 306 can include processor 316 and memory 318. Memory 318 includes (e.g., may be encoded with) executable instructions 320 for detecting product loss or tracking weight and water activity. The memory 318 can comprise a non-transitory computer-readable medium having instructions 320 stored therein or encoded thereon. Water activity meter 310 can include a controller and sensors. It should be understood that system 300 shown in FIG. 3 is an example of one suitable architecture for implementing certain aspects of the present disclosure. Additional, fewer, and/or different components may be used in other examples. It should be noted that implementations of the present disclosure are equally applicable to other types of devices such as mobile computing devices and devices accepting gesture, touch, and/or voice input. Any and all such variations, and any combination thereof, are contemplated to be within the scope of implementations of the present disclosure. Further, although illustrated as separate components of computing device 306, any number of components can be used to perform the functionality described herein. Although illustrated as being a part of computing device 306, the components can be distributed via any number of devices. For example, processor 316 can be provided via one device, sever, or cluster of servers, while memory 318 may be provided via another device, server, or cluster of servers.

As shown in FIG. 3, computing device 306, scale/balance 308, and water activity meter 310 may electronically communicate with each other via network 302, which may include, without limitation, one or more direct connections, local area networks (LANs), and/or wide-area networks (WANs). Such networking environments are commonplace in offices, enterprise-wide computer networks, laboratories, homes, intranets, and the Internet. Accordingly, network 302 is not further described herein. It should be understood that any number of computing devices, sensors, and/or meters may be employed within system 300 within the scope of implementations of the present disclosure. Each may comprise a single device or multiple devices cooperating in a distributed environment. For instance, computing device 306 could be provided by multiple server devices collectively providing the functionality of computing device 306 as described herein. Additionally, other components not shown may also be included within the network environment. In some embodiments, the individual components may electronically communicate directly with each other.

Computing device 306, sensor 308, and water activity meter 310 may have access (e.g., via network 302) to at least one data store or repository, such as data store 304, which may include any data related to weight data, water content data, temperature data, water activity data, product property data, as well as any associated metadata therewith. Data store 304 may further include any data related to techniques or executable instructions for calculating water content, water weight changes, non-water weight changes, product properties, control signals, and indicator signals. In implementations of the present disclosure, data store 304 may be searchable for its data and techniques or executable instructions described herein.

Such information stored in data store 304 may be accessible to any component of system 300. The content and volume of such information are not intended to limit the scope of aspects of the present technology in any way. Further, data store 304 may be a single, independent component (as shown) or a plurality of storage devices, for instance, a database cluster, portions of which may reside in association with computing device 306, scale 308, water activity meter 310, another external computing device (not shown), and/or any combination thereof. Additionally, data store 304 may include a plurality of unrelated data repositories or sources within the scope of embodiments of the present technology. Data store 304 may be local to computing device 306, scale 308, or water activity meter 310. Data store 304 may be updated at any time, including information about water activity to water content conversion of various products, isotherms, measurements, historical weight, water activity, or water content data, etc.

Examples of the scale 308 described herein may generally implement the collection of weight or mass data. In some embodiments, the scale 308 may be located within a processing plant, such as within a batch processing center for drying, bucking, trimming, burping, curing, sorting, or packaging a product. In some embodiments, the scale 308 is one of a plurality of scales or balances capable of collecting weight and mass data distributed throughout the system 300 (e.g., distributed throughout a processing plant). In some embodiments, the scale 308 can comprise a load cell, a mechanical scale, a spring-based scale, a hydraulic or pneumatic scale, a strain gauge-based scale, an elastic scale, related devices, and combinations thereof. A single scale 308 can be used to take a weight measurement of a product batch before it is processed and to take a weight measurement after it is processed, or multiple scales can be used to obtain different weight measurements.

A water activity meter 310 can be used to implement the collection of water activity data. In some embodiments, the water activity meter 310 can comprise sensors for detecting the temperature, weight, vapor pressure, and related properties of a sample of the product that is taken from a batch of the product and placed into a closed chamber of the water activity meter 310. The closed chamber can comprise a controlled-pressure, controlled-temperature chamber. In some embodiments, the water activity meter 310 can detect when water vapor pressure of the interior of the closed chamber is equal to (or in equilibrium with) the vapor pressure of the sample of the product and then determine the water activity of the product based on a database of isotherms for the product related to the water content of the product (e.g., information stored by the data store 304).

Examples herein may include computing devices, such as computing device 306 of FIG. 3. Computing device 306 may in some examples be integrated with one or more sensors (e.g., scales and/or water activity meters) described herein. Computing device 306 may further be centralized, e.g., not integrated with one or more sensors described herein. In some examples, computing device 306 may be implemented using one or more computers, servers, smart phones, smart devices, or tablets. Computing device 306 may facilitate improved weight and water content change tracking. Computing device 306 may include computer readable media encoded with executable instructions (e.g., 320) and a processor 316 that may execute the instructions to provide for power system stabilization and oscillation damping control. As described herein, computing device 306 includes processor 316 and memory 318. Memory 318 may include executable instructions for weight and water content change tracking or product loss detection. In some embodiments, computing device 306 may be physically coupled to scale 308 and/or water activity meter 310 (e.g., the components may be integrated and/or may be connected using a wired interface, such as bus, interconnect, board, etc.). In other embodiments, computing device 306 may not be physically coupled to scale 308 and/or water activity meter 310 but collocated with the scale and/or the water activity meter. In even further embodiments, computing device 306 may neither be physically coupled to scale 308 and/or water activity meter 310 nor collocated with the scale 308 and/or water activity meter 310. Data provided by the scale 308 or water activity meter 310 may be stored in a location accessible to other components in the system in some examples.

While a single scale 308 and water activity meter 310 are shown in FIG. 3, any number may be used. In some embodiments, a single instrument can be used to perform the functions of the scale 308 and water activity meter 310. Additionally, systems described herein may include multiple sensors distributed throughout the system. In some examples, sensors may be provided for each processing area in the system 300, such as in each processing area in a production plant. In some examples, sensors may be provided for a representative sample of processing areas in the system (e.g., in at least 10 percent of a certain type of processing area in the system in some examples, at least 20 percent in some examples, at least 30 percent in some examples, at least 40 percent in some examples, at least 50 percent in some examples, at least 60 percent in some examples, at least 70 percent in some examples, at least 80 percent in some examples, at least 90 percent in some examples). Thus, a representative sample number of processing areas can be equipped with sensors to maximize efficiency of using the sensors for their intended purposes.

Computing devices, such as computing device 306 described herein may include one or more processors, such as processor 316. Any kind and/or number of processor may be present, including one or more central processing unit(s) (CPUs), graphics processing units (GPUs), other computer processors, mobile processors, digital signal processors (DSPs), microprocessors, computer chips, and/or processing units configured to execute machine-language instructions and process data, such as executable instructions 320. A computing device 306 can also comprise other computer components (not shown) to operate and interconnect the computing device 306, such as, for example, an input/output controller, a display or other output device, input devices, network interfaces, etc.

Computing devices, such as computing device 306, described herein may further include memory 318. Any type or kind of memory may be present (e.g., read only memory (ROM), random access memory (RAM), solid state drive (SSD), and secure digital card (SD card). While a single box is depicted as memory 318, any number of memory devices may be present. The memory 318 may be in communication (e.g., electrically connected) to processor 316.

Memory 318 may store executable instructions for execution by the processor 316, such as executable instructions 320 for determining water weight changes and non-water weight changes of a product. Processor 316, being communicatively coupled to scale 308 and water activity meter 310, and via the execution of executable instructions 320 for determining water weight changes and non-water weight changes of a product, may track changes for a product based on collected data from the scale 308 and water activity meter 310.

Figure 4:
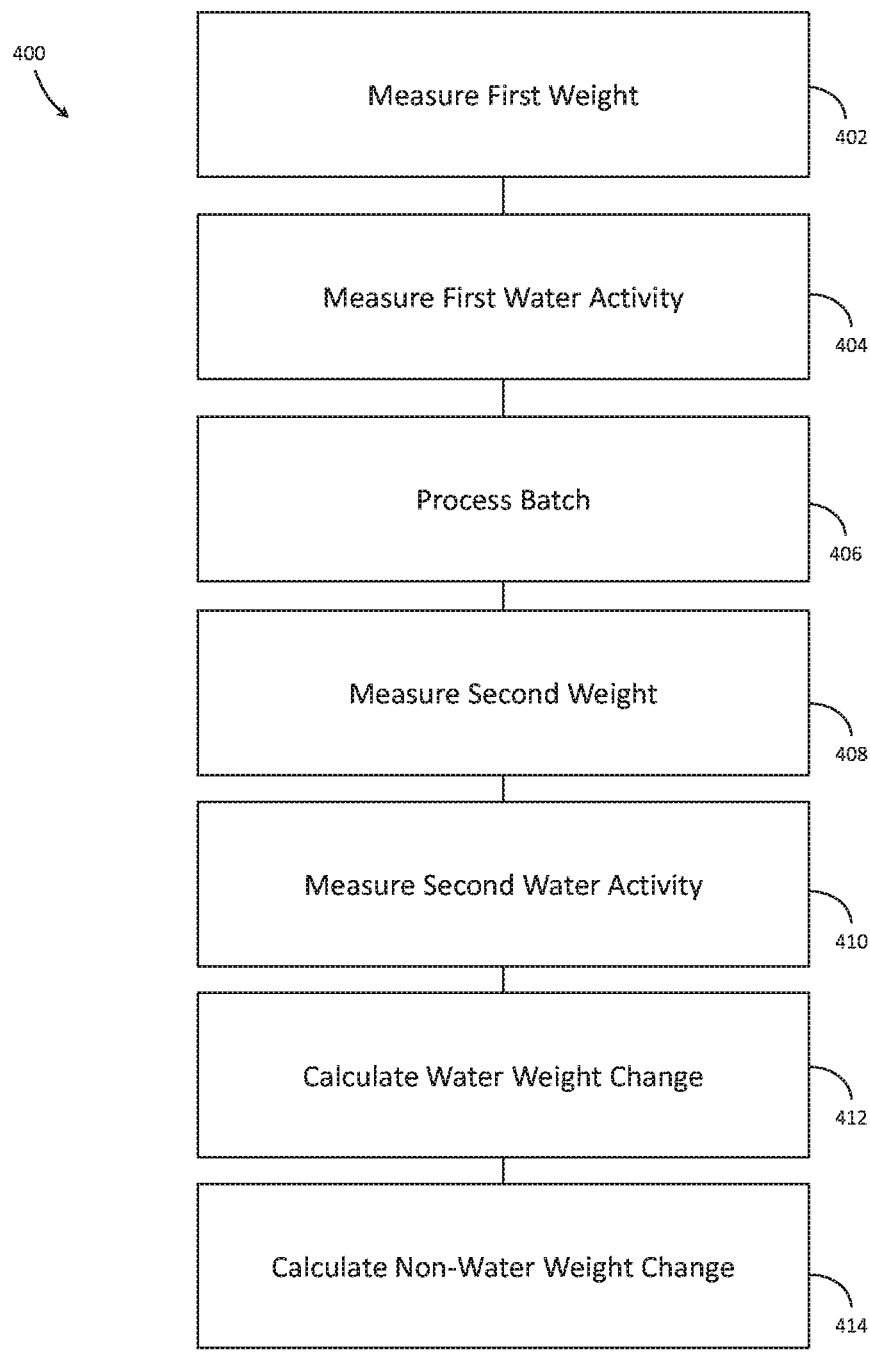
FIG. 4 is a process diagram of a process for tracking and determining the nature of changes to a product as it is processed.

FIG. 4 illustrates a diagram of a process 400 for determining water weight changes, non-water weight changes, and generating associated signals related to a product being processed over time. In some embodiments, this process 400 can be implemented as part of the executable instructions 320 of the system 300. The process 400 can comprise measuring a first weight value of a product in a first span of time, as indicated in block 402. The first weight value can be measured by a weight sensor such as a scale 308 or water activity meter 310. In some embodiments, a batch of the product, such as multiple pounds of the product, can be weighed together using the sensor. The first weight value can include the weight (e.g., in pounds) or mass (e.g., in kilograms) of the product. In some embodiments, the first weight value can be referred to as a wet weight, an original weight, a starting weight, or preprocessing weight. Generally, the first weight value can include the initial water weight and the initial non-water weight of the product combined. The first weight value can correspond to the original product weight 100 of FIG. 1 or 2.

The first span of time can refer to a period of time preceding the processing of the product that takes place in block 406, as explained in further detail below. Thus, the first span of time can include a point in time preceding the processing of the product or can include a short length of time (e.g., within a range of about 1 to about 30 minutes) in which both the product's weight and water activity values are measured. The weight and water activity values collected in the first span of time, such as within blocks 402 and 404, can beneficially be taken within a period of time wherein water weight loss from the product over the span of time is negligible so that the first weight value and first water activity value correspond to substantially the same product (i.e., product that has not undergone significant changes in its physical characteristics between measuring the weight value and the water activity value).

The process 400 can further include measuring a first water activity value of the product in the first span of time, as indicated in block 404. The first water activity value can be measured using a water activity meter such as water activity meter 310 in FIG. 3. Measuring the first water activity value can comprise removing a portion or sample of the product from the batch of the product weighed in block 402, placing the sample in a chamber of a water activity meter, and measuring the water activity of the sample. The water activity value of the sample may be representative of the water activity of the batch as a whole, and, in some embodiments, the sample can be discarded after testing. In some embodiments, the water activity can be measured by obtaining information about the temperature and vapor pressure of the product sample at equilibrium in the water activity meter 310, and the measurements taken can be directed to a computing device (e.g., device 306 via network 302) to process the information and convert the raw data collected into water activity and water content measurements. The water activity and water content measurements can correspond to a water weight value of the product sample such as, for example, the proportion of the weight of the product sample that is attributable to water content in the product sample. Once the water weight of the product is known, the non-water weight can be calculated as the remaining weight of the product sample. The properties of the sample can then be applied to the rest of the batch so that the water weight and non-water weight can be established for of the entire batch weighed in block 402.

After measuring the first weight and first water activity values, the batch of product can be processed or altered, as indicated in block 406. Processing the product can include drying the batch of the product, curing the batch, dividing the batch, trimming the batch, separating one portion of the batch from another (e.g., separating cannabis leaves from buds), cooking the batch, heating or cooling the batch, washing the batch, applying a similar process (e.g., other processes described herein), or combinations thereof. The batch can therefore undergo changes to its physical and chemical characteristics as a result of the processing in block 406. In some embodiments, these changes can include directly or indirectly removing or adding water to the batch of product and thereby increasing or decreasing the water activity or water content of the product as it is processed.

Next, within a second span of time following the processing stage, a second weight and second water activity value can be measured for the product, as shown in blocks 408 and 410. The second span of time can occur later than the first span of time, such as, for example, during or at the end of the processing of the batch in block 406 and can have a duration similar to the first span of time, wherein the batch of the product does not undergo significant water weight changes while the second weight value and second water activity value are collected. The measurement of the second weight and second water activity value can be conducted using the same techniques and instruments described above in connection with blocks 402 and 404, respectively. For example, the second weight value can be obtained by measuring the weight of the batch remaining at the second span of time, and the second water activity value can be obtained by taking a small sample from the batch at the second span of time and obtaining its water activity using a water activity meter.

In most cases, the second weight and second water activity value will differ from the first weight and the first water activity value. As explained elsewhere herein, this can be a natural result of the process undertaken in block 406, the humidity or other environmental conditions of the area in which the process of block 406 is undertaken, the sampling process or natural errors or waste generated by the measurement or processing acts, or product loss. In order to differentiate between the different types of changes to the weight and water content of the batch, the process 400 can further include calculating a water weight change in block 412. The water weight change can be calculated by obtaining the water weight of the product within the first and second weights measured in blocks 402 and 408 based on the first and second water activity values measured in blocks 404 and 410. The water weight change can be defined as the difference between the water weight portion of the first weight value and the water weight portion of the second weight value. The non-water weight change, calculated in connection with block 414, can be determined by finding the difference between the remainder of the first weight value (after removing or subtracting the water weight in the first weight value) and the remainder of the second weight value (after removing or subtracting the water weight in the second weight value).

For instance, the first and second water activity values can be converted into water content values representative of the proportion of the weight made of water in the batch of the product at the first and second spans of time. This conversion can be made based on data that is collected empirically and in advance for whichever type of product is being processed in connection with process 400. For example, for cannabis, the water content of various batches of product can be determined for various water activity values measured in each batch at different temperatures. Those water activity values, temperatures, and water content values can be correlated and tabulated so that when future temperature and water activity measurements are taken for cannabis, the water content can be determined or reliably and quickly extrapolated or inferred from the previous measurements. The correlated and tabulated information can be electronically accessible (e.g., with data store 304 connected via network 302) and can therefore be substantially instantaneously accessible as the process 400 is performed. The information can be stored for a plurality of different types of products (or byproducts) being processed at a plant, other plants, or other facilities having their products being tracked and monitored by the system. Thus, the database can comprise information regarding the water activity, water content, and temperature(s) of those measurements so that they can be accessed to determine the water content in relation to measured water activity and temperature of a product sample in connection with block 412.

In some embodiments, a change in the non-water weight, as calculated in block 414, can be compared to stored data. The stored data can include historical data about batches of the product being processed at the facility. For instance, the historical data can include information about the change in non-water weight for previous batches of product in the facility for one or more processing acts being performed on the product. This historical data can indicate a baseline or standard acceptable threshold of non-water weight change for the product as it is being processed. In some embodiments, the data can also be correlated with plant location, its environment, the source of the product, the different workers or machines processing the product, and other related information. Therefore, in some embodiments, the process 400 can further include comparing the change in water weight or the change in non-water weight, in real time, to a set of data or a threshold limit value to help detect anomalies in the changes in water or non-water weight as the product is being processed. For example, if a change in the non-water weight is larger in magnitude than one standard deviation (or another relative threshold value) of the historical changes in non-water weight, the processing of that batch can be flagged, investigated, or tracked to detect the source of the product loss. If a change in the non-water weight is positive/greater than zero or some other numeric threshold (i.e., indicating that mass was created during the process), that process can be flagged or investigated as well. If a change in the non-water weight is less than the relative threshold value, such as the routine changes in non-water weight that are attributable to sampling and testing the product, losing small parts of it to waste or product deterioration, or losing weight accuracy due to measurement or calculation error, the processing of that batch can be treated as normal or within acceptable bounds of operation.

A computing device (e.g., 306) can compare these large data sets to newly-collected weight data nearly instantaneously and in real-time so that plant operators, regulators, or other supervisors can identify and react quickly to potentially problematic incidents. In some configurations, a plant worker attempting to improperly interfere with the measurements can be identified substantially immediately after the second weight value and second water activity value are measured, thereby allowing supervisors or security to investigate the missing product before the worker has time to abscond with stolen material.

Furthermore, in some embodiments, a computerized system can be used to receive input data including the first and second weight values and the first and second water activity values, and the computerized system can conceal or hide the results of the calculations of the changes to water or non-water weight from the worker providing the data to the system. In some embodiments, the worker/operator is kept from knowing that a water activity measurement is being gathered at all. For example, the measurements can be gathered without the computing device making those measurements accessible to the operator. In this manner, a person attempting to manipulate the results of the weighing or water activity measurement tests can be prevented from receiving feedback and learning in real-time whether their attempts to interfere with the system are being detected or not. Therefore, supervisors can be permitted to collect additional data and evidence, if needed, without alerting the operator and inducing a change in behavior.

In some embodiments, the process 400 can further include generating, sending, or producing a signal representative of a change in water weight, a change in non-water weight, the first or second weight values, the first or second water activity values, or the first or second water content values. The signal can be transmitted or sent using a network (e.g., network 302). For changes in weight, the signal can indicate the value of the difference in weight, can indicate that the difference exceeds a threshold or acceptable range of values, can indicate that a difference exists, or can provide another related indication. The signal can then be converted into an alert, an alarm, or another indicator of whether the signal indicates a potential problem or a normal or expected value.

Figure 5:
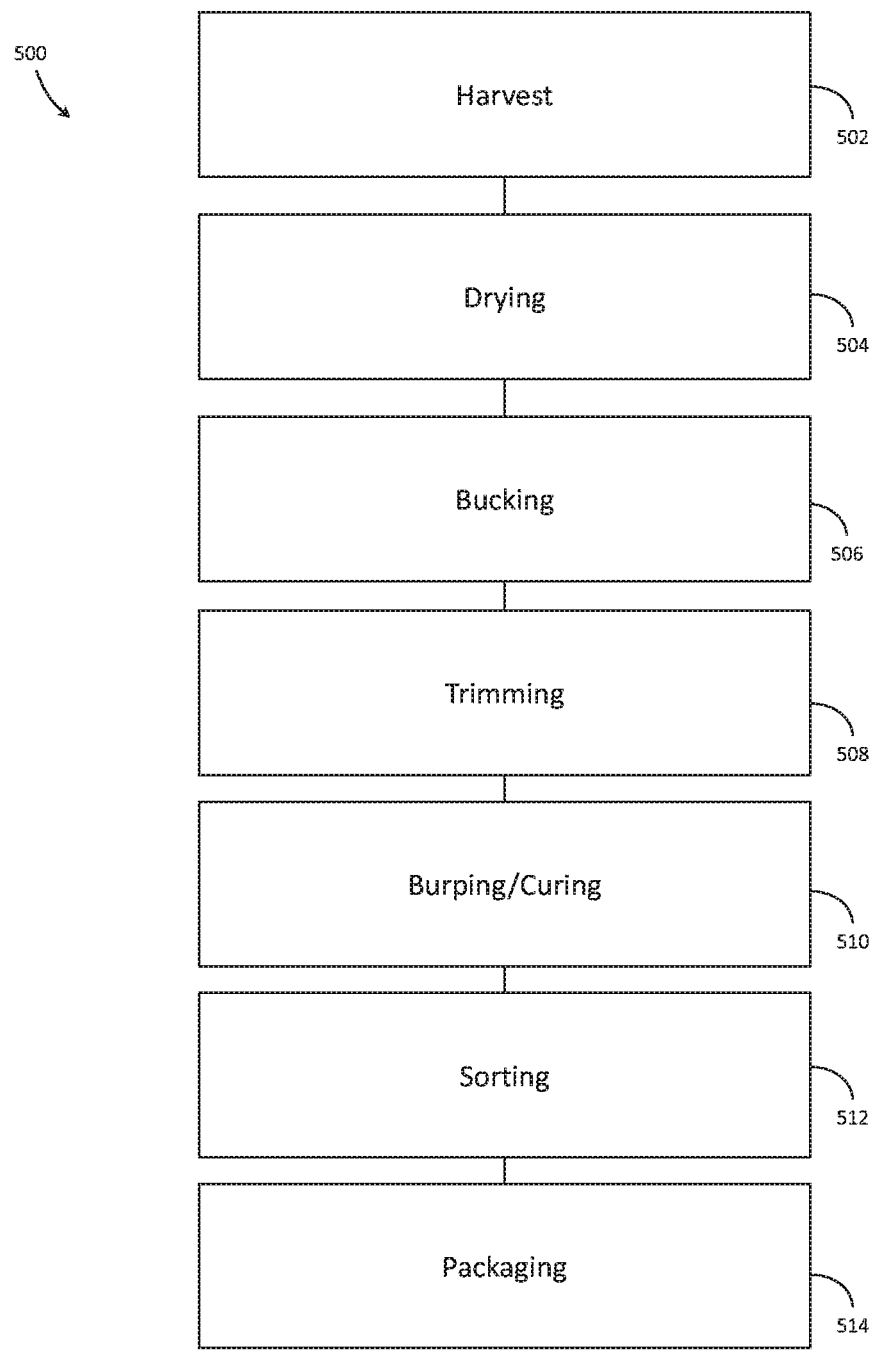
FIG. 5 is a process diagram of various stages that a product can pass through while being processed in embodiments of the present disclosure.

The process 400 can be performed multiple times throughout the overall processing stages of a batch of a product over time. FIG. 5 shows an example embodiment of a plurality of stages 500 through which an example product (e.g., cannabis) can be processed while undergoing the process 400 multiple times. For example, the stages 500 can include a harvesting stage 502 in which the product is harvested, collected, and transferred to a processing facility. In some embodiments, one or more batches of the product can be weighed (e.g., as in block 402) and can have their water activity measured (e.g., as in block 404). For example, the product can be measured in this manner when it is collected into bundles or shipping containers before reaching a processing facility, and then can be measured again (e.g., as in blocks 408 and 410) after being transported to the facility or after being divided into batches at the facility (i.e., after being processed according to block 406). Calculations (e.g., under blocks 412 and 414) and signals can be generated for the harvesting stage 502 to monitor the status of the product over the time it is undergoing the harvesting process (i.e., from a first span of time in which the product is being collected to a second span of time in which the product is unloaded or divided into batches at the facility) and to determine changes in the water and non-water weight of the product.

The stages 500 can also include a drying stage 504, a bucking stage 506, and a burping/curing stage 510 that can have respective first weight and water activity measurements at their starting points and respective second weight and water activity measurements of the same bundle or batch of product at their ending points. Changes in water weight and non-water weight can also be determined, analyzed, and responded to along the way. At a trimming stage 508 or sorting stage 512, the product can be further divided into component parts or byproducts (e.g., trimming leaves from buds or sorting bud sizes into categories), and weight and water activity measurements can be collected for the initial product (i.e., before it is divided) and separately for each of the post-processed products (i.e., the buds and leaves or the different bud groups). The total water weight can be compared to the total non-water weight at the start and finish, and each of the post-processed products can have their own error/waste/normal loss thresholds used for generating alerts and potential loss signals. In other words, one set of final components (e.g., the leaves) can have a greater variation threshold for identifying problematic data than another set of final components (e.g., the buds). Different calibration curves can be used for different types of products and byproducts to account for different water sorption characteristics.

In a packing or packaging stage 514, the product can be packaged for delivery to a consumer. A measurement of the weight and water activity of the product can be obtained upon check-in of the product at the packaging stage 514. The product can then be packaged and sealed for shipping. In order to confirm weight and water activity after packaging, the packaged product can be weighed and sampled (e.g., at least partially taken from a package) for water activity testing. Thus, the product's weight and water activity can be used to track the status and nature of weight changes of the product in the packaging stage 514 as well. In this manner, operators and supervisors can better detect losses of product and other inefficiencies in processing operations and can thereby save money, improve systems, and overcome other operational challenges described herein.

Various inventions have been described herein with reference to certain specific embodiments and examples. However, they will be recognized by those skilled in the art that many variations are possible without departing from the scope and spirit of the inventions disclosed herein, in that those inventions set forth in the claims below are intended to cover all variations and modifications of the inventions disclosed without departing from the spirit of the inventions. The terms "including:" and "having" come as used in the specification and claims shall have the same meaning as the term "comprising."

What is claimed is:

1. A method, comprising:
    measuring a first weight value of a product in a first span of time;
    measuring a first water activity value of the product in the first span of time;
    measuring a second weight value of the product in a second span of time, the second span of time being after the first span of time;
    measuring a second water activity value of the product in the second span of time;
    determining a change in water weight of the product between the first span of time and the second span of time based on the first and second water activity values;
    determining a change in non-water weight of the product between the first span of time and the second span of time based on the first and second weight values of the product and based on the change in water weight of the product; and
    detecting a loss indicator of the product based on the change in non-water weight of the product.

2. The method of claim 1, further comprising altering the product between the first and second spans of time.

3. The method of claim 2, wherein altering the product comprises drying the product.

4. The method of claim 2, wherein altering the product comprises dividing the product.

5. The method of claim 2, wherein altering the product comprises curing the product.

6. The method of claim 1, wherein measuring the first or second water activity value comprises removing a sample portion from the product and measuring a water activity of the sample portion.

7. The method of claim 1, wherein a user operates tools to measure the first weight value, the first water activity value, the second weight value, and the second water activity value, and wherein the method further comprises hiding at least the change in non-water product weight from the user.

8. The method of claim 1, further comprising producing a signal representative of the change in non-water weight.

9. The method of claim 1, further comprising positioning the product in a closed chamber for the first span of time or the second span of time.

10. A non-transitory computer-readable medium having computer-executable instructions stored thereon that, if executed by one or more processors of a computing device, cause the computing device to perform a method comprising:
    receiving a first weight value of a product for a first span of time;
    receiving a first water activity value of the product for the first span of time;
    receiving a second weight value of the product for a second span of time, the second span of time being after the first span of time;
    receiving a second water activity value of the product for the second span of time;
    determining a change in water weight of the product between the first span of time and the second span of time based on the first and second water activity values;
    determining a change in non-water weight of the product between the first span of time and the second span of time based on the first and second weight values of the product and based on the change in water weight of the product; and
    detecting a loss indicator of the product based on the change in non-water weight of the product.

11. The computer-readable medium of claim 10, wherein the product is altered between the first and second spans of time.

12. The computer-readable medium of claim 10, wherein the first or second water activity value is a water activity value of a sample portion of the product.

13. The computer-readable medium of claim 10, wherein the method further comprises hiding the change in non-water weight from a user who obtains the first weight value, the first water activity value, the second weight value, or the second water activity value.

14. The computer-readable medium of claim 10, wherein the method further comprises producing a signal representative of the change in non-water weight.

15. A computing device, comprising:
    a processor;
    a memory device comprising computer-executable instructions that, if executed by the processor, cause the computing device to perform a method comprising:
        receiving a first weight value of a product for a first span of time;
        receiving a first water activity value of the product for the first span of time;
        receiving a second weight value of the product for a second span of time, the second span of time being after the first span of time;
        receiving a second water activity value of the product for the second span of time;

determining a change in water weight of the product between the first span of time and the second span of time based on the first and second water activity values;

determining a change in non-water weight of the product between the first span of time and the second span of time based on the first and second weight values of the product and based on the change in water weight of the product; and hiding the change in non-water weight from a user who obtains the first weight value, the first water activity value, the second weight value, or the second water activity value.

16. The computing device of claim 15, wherein the first or second water activity value is a water activity value of a sample portion of the product.

17. The computing device of claim 15, wherein the method further comprises producing a signal representative of the change in non-water weight.

18. The computing device of claim 15, wherein the method further comprises detecting a loss indicator of the product based on the change in non-water weight.

* * * * *